United States Patent [19]

Siekhaus

[11] Patent Number: 4,667,101
[45] Date of Patent: May 19, 1987

[54] PREDICTING THRESHOLD AND LOCATION OF LASER DAMAGE ON OPTICAL SURFACES

[75] Inventor: Wigbert Siekhaus, Berkeley, Calif.

[73] Assignee: The United States of America as respresented by the United States Department of Energy, Washington, D.C.

[21] Appl. No.: 697,828

[22] Filed: Feb. 4, 1985

[51] Int. Cl.[4] .......................................... G01N 23/227
[52] U.S. Cl. .................................... 250/307; 250/306; 250/492.1
[58] Field of Search ............. 250/306, 307, 288, 492.1

[56] References Cited

U.S. PATENT DOCUMENTS

| 3,999,865 | 12/1976 | Milam et al. | 356/239 |
| 4,096,386 | 6/1978 | Rempfer et al. | 250/311 |
| 4,208,585 | 6/1980 | Vogt | 250/288 |
| 4,330,208 | 5/1982 | Eloy | 250/288 |
| 4,385,832 | 5/1983 | Doi et al. | 356/73.1 |

OTHER PUBLICATIONS

Endert et al., *Soviet Journal of Quantum Electronics*, 7 (12), Dec. 1977, pp. 1516–1518.
Batyreva et al., *Soviet Journal of Quantum Electronics*, 8 (8), Aug. 1978, pp. 1044–1046.
Krasnotsvetova et al., *Soviet Journal of Quantum Electronics*, vol. 4, No. 1, Jul. 1974, p. 125.
Wang et al., *Laser Induced Damage in Optical Materials:* 1974, pp. 59–65.
Van Stryland et al., *Laser Induced Damage in Optical Materials:* 1977, pp. 118–126.
Temple et al., *Laser Induced Damage in Optical Materials:* 1979, pp. 229–236.

*Primary Examiner*—Bruce C. Anderson
*Assistant Examiner*—Jack I. Berman
*Attorney, Agent, or Firm*—Charles E. Lykes, Jr.; Clifton E. Clouse, Jr.; Judson R. Hightower

[57] ABSTRACT

An apparatus useful in the prediction of the damage threshold of various optical devices, the location of weak spots on such devices and the location, identification, and elimination of optical surface impurities comprising, a focused and pulsed laser, an photo electric detector/imaging means, and a timer. The weak spots emit photoelectrons when subjected to laser intensities that are less than the intensity actually required to produce the damage. The weak spots may be eliminated by sustained exposure to the laser beam.

11 Claims, 4 Drawing Figures

PREDICTING THRESHOLD AND LOCATION OF LASER DAMAGE ON OPTICAL SURFACES

The invention described herein arose in the course of, or under, Contract No. W-7405-ENG-48 between the United States Department of Energy and the University of California.

BACKGROUND OF THE INVENTION

The present invention relates to the examination of optical devices for weak spots, or damage prone areas, particularly when the weakness is due to an impurity on the optical surface.

Modern day applications of laser devices call for increasingly powerful and precise beams. Such applications require high resolution optical devices such as lenses, filters, and mirrors. The application of large intensities of laser energy to these devices frequently destroys them during operation. Often the level of intensity required for experimental applications (such as the Projects Nova and Novette at the Lawrence Livermore National Laboratory) is so high that pretesting of the optical device at the required intensities would be impractical. The level of effort required to prepare for and execute the desired experiments, however, is very high and so an effective means of pretesting such devices is desirable.

Presently there are no commercially available devices capable of "stress testing" a particular optical device. U.S. Pat. No. 3,999,865, issued Dec. 28, 1976 to Milam, et al, teaches an instrument capable of analyzing the cause of damage to optical devices. It provides for subjecting the device to a damaging energy and intensity and then analyzing the damage from the standpoint of time and applied power in order to determine the one or more of several reasons for the laser induced damage. While Milam is helpful in improving system design or production techniques, it requires that damage actually occur and only indirectly identifies flaws through analysis of the parameters of the damaging event. The tested device clearly can no longer be used.

THEORY OF THE INVENTION

The inventor has used two effects to devise a means for pre-testing and analyzing individual optical devices in order to determine whether or not they will be able to handle the electromagnetic energies and intensities required for a particular planned use and to identify impurities on the optical surface. The first effect is that damage to optical devices occurs to their surfaces first. While there is no certain explanation for this, it has been experimentally verified and is widely accepted as accurate (see NBS Special Publication 620, Laser Induced Damage in Optical Materials: 1980, Bennet et al).

The second effect, and one discovered by the inventor, is that "weak" or damage prone spots of an optical surface will emit photoelectrons, when subjected to laser beam intensities from one to several orders of ten less than that required to actually produce the damage. FIG. 1 is a graph reflecting data obtained by the inventor demonstrating this effect. The figure contains a graph with two curves plotting net emitted photoelectron charge versus incident laser intensity from two different optical surfaces. The first, labeled ZnS, having emission represented by small squares, was a zinc sulfide (ZnS) optical surface. The second, labeled $SiO_2$, having emission represented by small circles, was a silicon quartz ($SiO_2$) optical surface.

The two curves both demonstrate three general regions, marked 4, 5, and 6. In region 4, the surfaces are first beginning to emit photoelectrons. At a greater laser intensity, at region 5, the curves begin to level off. This is because the greater laser intensity is beginning to form a plasma from the surface impurity or structural irregularity and release positively charged photo-ions as well, cancelling some of the negative photoelectron charge. (Hereinafter photo-ion will be meant to refer to positively charged photo-ions only.) At region 6 both surfaces experience damage as the increased particle emission breaks down the molecular structures on the optical surfaces. For the ZnS surface, the initial photoelectron emission was about 1.8 orders of ten below the damage threshold. For the $SiO_2$ surface the initial emission was somewhat closer, or about 0.8 orders of ten below the damage threshold of the optical surface.

The use of adjustable electric or magnetic fields, as described in "Electron Emission Microscopy", G. Mollenstadt, et al, pp 251–329 *Advances in Electronics and Electron Physics,* Volume 18, 1963, makes it possible to usefully control the photoelectric emission from a given surface, such as an optical surface. Emitted photoelectrons and photo-ions may thus be directed at detectors by adjustable electric field strengths, or may be projected to some form of high resolution imaging device in order to pinpoint the locations from which emission has occurred.

With the proper instrumentation and data then, it is possible to predict, with respect to a given optical surface, where and at what level of laser intensity damage will begin to occur on the surface. This intensity, then, is the laser damage threshold of the optical device. Additional examination may be conducted to further identify or explain the weakness in the device, particularly when the weakness is the result of a surface impurity. With such information, defective optical devices can be improved or replaced and experimentation or operation begun without fear of optical device failure.

SUMMARY OF THE INVENTION

The inventor has combined the phenomena and principles described above into several embodiments to provide methods and associated apparatus for pre-testing optical devices for operation at particular wavelengths and intensities.

In the simplest embodiment of the invention laser-induced photoelectron emission is used to determine the damage threshold of the optical device. Laser-induced photoelectron emission may also be used to locate the weak spots on the optical surface. By stimulating photo-ion emission with a laser, embodiments are possible which identify and purge impurities from the optical surface.

An advantage of the invention is its ability to perform the described functions without causing damage to the optical surface. This is because laser intensities below the damage threshold are all that are required to perform them. This permits the optical surface to be cleared for use at a given intensity without ever having been exposed to that intensity.

Another advantage of the invention is that only a relatively small amount of power, when compared with the power at which operation is to be accomplished, is required to perform the pre-testing. This is because the requisite laser intensities may be developed by focusing a relatively weak laser into a small area and examining the optical surface by probing it with this focused beam in small increments.

It is, then, an object of the invention to provide a means for thoroughly examining an optical surface for the location and identification of weak spots or surface impurities without damaging the optical device.

It is a further object of the invention to determine the mass to charge ratio of impurities on an optical surface.

It is a further object of the invention to provide a means for the extraction of optical surface impurities in order to improve the performance of the optical device.

It is a further object of the invention to provide a simple stress test of an optical device by examining its surface for the presence of areas with a damage threshold below that for which use of the device is anticipated.

Other objects and advantageous features of the invention will be apparent in a description of a specific embodiment thereof, given by way of example only, to enable one skilled in the art to readily practice the invention which is described hereinafter with reference to the accompanying drawings.

DETAILED DESCRIPTION

Figure 1:
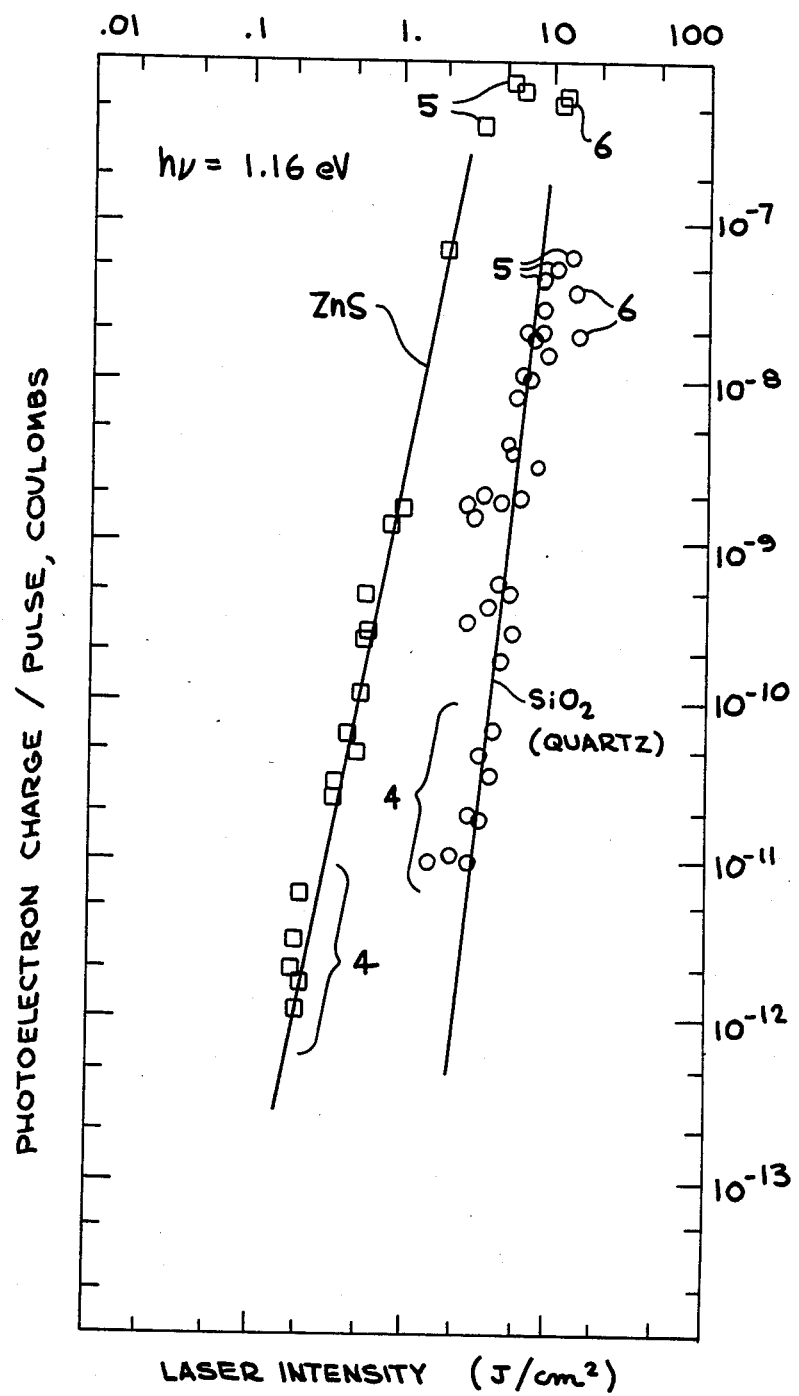
FIG. 1 is a graph demonstrating the regions of initial photoelectron emission, initial photo-ion emission, and initial damage to optical surfaces made from both zinc sulfide and quartz.

Reference will now be made in detail to the present preferred embodiments of the invention, examples of which are illustrated in the accompanying drawings.

While the invention will be described in connection with its preferred embodiments, it will be understood that it is not intended to limit the invention to those embodiments. On the contrary, it is intended to cover all alternatives, modifications, and equivalents as may be included within the spirit and scope of the invention as defined in the appending claims.

Herein described is an invention useful in the examination of optical surfaces for "weak" spots due to structural imperfections or surface impurities and for the identification of surface impurities, when feasible. In fact the process may be used to perform final optical "cleansing" which may actually strengthen and improve the performance of the optical device as the process can be simply modified to extract the surface impurities.

In general, the invention includes a laser beam of wavelength near that for which the device is being tested which is capable of adjustment, by focusing if necessary, to an intensity about $10^{-2}$–$10^{-1}$ of that at which the optical device is to be experimentally or functionally operated. The incident optical surface is mounted rigidly such that the plane of this surface is generally perpendicular to the laser beam. The laser beam and optical device configuration permit precise and controlled direction of the beam upon the incident optical surface.

The invention additionally includes an imaging apparatus and an adjustable photoelectric detector which may be used to detect either photoelectrons or photo-ions. The photoelectric detector and the optical surface is housed within a common vacuum and in an area free of any undesired electric or magnetic fields. The photoelectric detector is positioned such that there is an unobstructed path between it and the optical surface upon which the laser is incident and at a known distance from this surface.

The invention also includes a timer capable of accurately measuring the very short time periods required for photo-ions and photoelectrons to travel from the optical surface to the photoelectric detector.

In one embodiment of the invention the apparatus is operated in two phases. In the first phase the entire optical surface is hit with a laser beam which is about $10^{-1}$–$10^{-2}$ the intensity of that for which operation of the device is desired and at or very near the wavelength at which operation is desired.

If it is impractical from a power perspective to supply a beam broad enough at the requisite intensity, then the beam may be focused as necessary to obtain the broadest beam possible at the desired intensity under existing power constraints. This focused beam may then be systematically scanned over the entire optical surface.

In either case, the photoelectric detector is positively charged in order to measure the electron emission which has been found to precede optical surface damage. An imaging device may be used to precisely pinpoint the location from which photoelectrons are emitted. During this first phase the objective is to locate these damage prone areas from their photoelectron emission.

During the second phase the objective becomes to determine the mass to charge ratio of ionic particles of the impurity in order to identify the impurity. During this phase the laser is focused such that its width at the optical surface is about $3-10 \times 10^{-6}$ m and of greater intensity than before. While the intensity requirement for this phase will vary according to the optical material and means of manufacture and preparation, it may generally be said to be within one order of ten greater than that producing the photoelectron emission. The beam duration is very short, on the order of 3–5 nanoseconds.

The beam is specifically directed at those points identified as damage prone during the first phase of operation. At this heightened intensity ionization and photo-ion emission occurs. By negatively charging the photoelectric detector, these emitted photo-ions will be attracted and measured. By timing the flight of the photo-ion from the optical surface to the detector, one can determine the mass to charge ratio of the ionized particle because the distance traveled, time of flight, and the electric field strength are known.

If a variable laser is used, it can be adjusted to the lowest intensity producing photo-ion emission and left there over a prolonged period of time. By so doing, these "impurity" photo-ions are electrically extracted from the optical surface. The optical device may then be retested in order to confirm improved resiliency to damage.

In another embodiment the invention may be used simply to examine the optical device for weak spots and to confirm reliability up to a certain laser intensity and at a specific wavelength. A laser beam at that wavelength may be focused to about $10^{-3}$ m at an intensity of $10^{-2}$–$10^{-1}$ that of desired operation. The photoelectric detector may then be positively charged to attract and detect photoelectron emission. The focused laser beam is then scanned thoroughly over the entire optical surface. If no significant photoelectron emission is noted, the optical device is thereby cleared for use as desired. Should photoelectron emission occur, either further testing may be conducted or an alternate device prepared.

Figure 2:
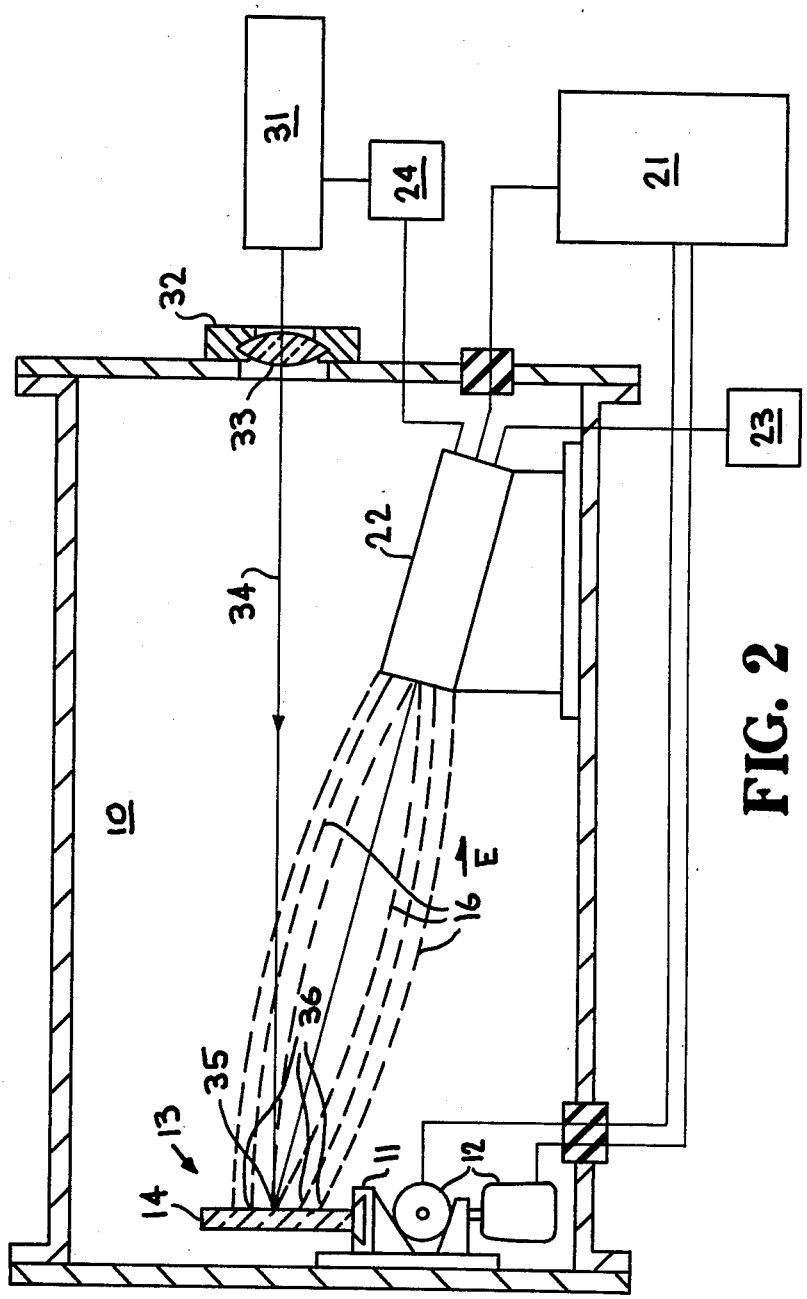
FIG. 2 is a schematic diagram of the basic device, showing the vacuum chamber, laser device, optical device mounting configuration, the photoelectric detector, recorder, and timer.

More specifically, a configuration of the first mentioned embodiment is schematically diagrammed in FIG. 2, the apparatus including a vacuum chamber 10, a laser device 31 with beam focusing means 32, a mount for the targeted optical surface 11, a photoelectric detector 22, with biasing means 23, and a timer 24.

The inventor has used a stainless steel vacuum chamber which is pumped down to $10^{-5}$ Torr. A Galileo model 6075 electron multiplier array is used as the photoelectric detector and a Tektronix 7612D timer performs the timing functions. Any adjustable photoelectric detector capable of detection of electron quantities of charge and timer capable of resolution to the order of a few nanoseconds may be utilized, however.

Within the vacuum chamber is a mount 11 for a target optical device 14. The mount 11 is oriented so that one surface 13 of the optical device 14 directly faces the laser window 33 and roughly faces a photoelectric detector 22. The mount 11 additionally is operably attached to a moving apparatus 12, so that it can be moved through the two dimensions (x and y) of the optical surface 13 such that the laser beam will be incident on all parts of the optical surface 13. The mount 11 is further operably connected to a recorder 21 which can record the position of the focused laser beam 34 on the target optical surface at a given point in time.

The photoelectric detector 22 can be adjusted, or biased, via a biasing means 23 to attract either photoelectrons or photo-ions and is variable so as to create the desired electric field strength. The photoelectric detector 22 is also operably connected with the recorder 21 such that the level of photoelectric emission at a given point in time may be recorded.

The laser device 31 may be mounted outside the vacuum chamber 10 and project its beam through a window 33 in the vacuum chamber 10. The laser device 31 is equipped with optical equipment 32 so as to permit the laser beam to be focused into a very intense narrow beam 34 of the order of 3–10$\times 10^{-6}$ m or into a less intense beam of $10^{-3}$ m. The laser device 31 is also designed to permit the production of a pulsed beam of only a new nanoseconds (3–5$\times 10^{-9}$ sec) duration. When operated in the pulsed configuration the laser device 31 is also operably connected to a timer 24 in order to note the instant of release of a laser pulse. When desired, the photoelectric detector 22 is also operably connected to the timer 24 such that the instant of arrival of a photoelectric particle, particularly photo-ions, may be noted.

The operation of this embodiment of the device is as follows.

First, the laser device 31 is adjusted and optically focused via lens 32 to produce a continuous beam 34 of about $10^{-3}$ m and of wavelength at or very near that for which operation of the target laser device 14 is expected. The intensity of this beam should be between $10^{-2}$ to $10^{-1}$ the intensity at which operation of the target optical device 14 is desired.

The target optical surface 13 then, is, by its moving apparatus 12, moved through the two axes (x and y) perpendicular to the laser beam 34 (roughly the plane of its surface 13) such that each part of the optical surface 13 has been exposed to the laser beam 34. The recorder 21 is set to record the part of the surface 13 exposed to the laser beam 34 at a given point in time.

The photoelectric detector 22 is adjusted to attract photoelectron emission and is also operably connected to the recorder 21 such that the photoelectron emission at a given point in time can be recorded. This permits the photoelectron emission to be examined as a function of position on the target optical surface 13 as both the laser beam 35 position and photoelectron emission at a given point in time are both known. From this data, then, the points of significant photoelectron emission are identified.

The laser device 31 is then adjusted to produce a pulsed beam of very short duration, of the order of a few nanoseconds (3–5$\times 10^{-9}$ sec). The optical system 32 of the laser is adjusted so as to focus the beam to only a very few micrometers (3–10$\times 10^{-6}$ m). The timer 24 is set to begin measuring time at the instant the laser pulse is produced.

The target optical surface 13, then, is moved by the moving apparatus 12 such that selected points 36 of significant photoelectron emission will be in the path of the focused laser beam as at 35. The photoelectric detector biasing system 23 is reversed to attract photo-ions and the electric field strength is carefully adjusted and measured 36. The timer 24 is operably connected to the photoelectric detector 22 to precisely measure the instant of arrival of a photo-ion at the detector.

An intense, focused laser pulse is then released at the point of significant photoelectron emission 35 and the timer 24 begins to measure a time interval. If the photoelectron emission was the result of a surface impurity, the intense laser beam 34 both ionizes and adds kinetic energy to the particles of the impurity. The negative electric field 36 from the photoelectric detector attracts the ionized particle with the force F=eE (where e is the charge on an electron and E is the electric field strength created by the photoelectric detector 22) until the particle reaches the photoelectric detector 22 and the timer 24 has measured the time interval between laser pulse and photo-ion detection, or time of flight of the particle.

The mass to charge ratio of the ionized particle may then be easily calculated from the mechanical relationships between Force (F), mass (m), acceleration (a), distance (d), and time (t) and the electrical relationships between charge (q), electric field strength (E), and force (F).

$$F = ma = qE \tag{1}$$

$$\frac{m}{q} = \frac{E}{a} \tag{2}$$

$$d = \frac{1}{2} at^2 \tag{3}$$

$$a = \frac{2d}{t^2} \tag{4}$$

then substituting 4 into 2

-continued
$$\frac{m}{q} = \frac{Et^2}{2d} \quad (5)$$

The assumption has been made in equation (3) that the particle starts from rest. It should also be noted that the charge, q, will always be an integral multiple of −e, where e is $-1.6 \times 10^{-19}$ coulombs, or the charge on a single electron.

If the mass of the photo-ion can be determined, its identity may be readily ascertained. A variety of methods may be used to determine the mass, including making deductions from the composition of the optical device or its environment or the application of magnetic fields to the moving particles in order to determine their exact charge.

It should be noted that the laser power required to operate this embodiment of the device is quite low when compared to that for which use of the optical device is being tested. This is because only a small part of the target optical surface 13 is being "observed" at a given time and so the required laser intensity can be developed by focusing a small amount of laser power into a small diameter.

Figure 3:
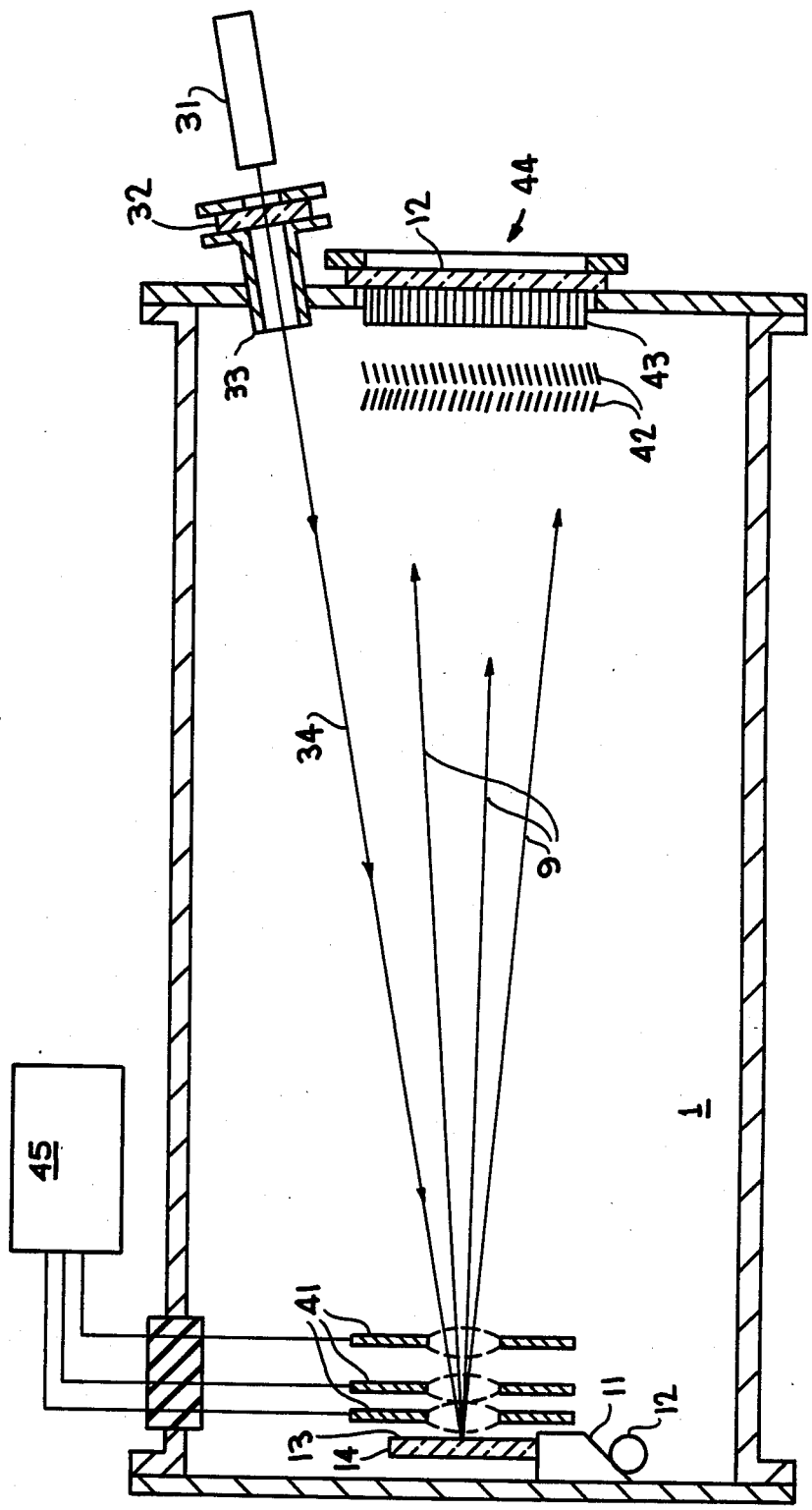
FIG. 3 is a schematic diagram of the high speed configuration, in which the recorder and photoelectric detector are replaced by the electrostatic imaging means.
Figure 4:
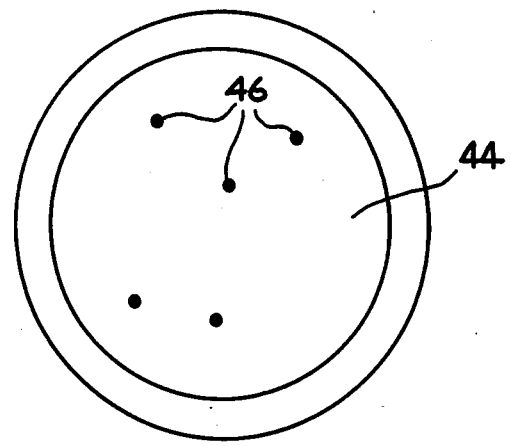
FIG. 4 is a diagram exemplifying the display of the electrostatic imaging means.

In a more time efficient embodiment of the device, the laser power requirement is much greater. This embodiment, depicted in FIG. 3, is capable of observing the entire optical surface 13 at once. An electrostatic imaging device according to FIG. 3 includes an electrostatic lens 41, an electron multiplier 42, a fiberoptic array 43, and a fluorescent screen 44.

In this embodiment of the device the target optical surface 13 is held steady while a more powerful laser beam 34 is focused by the optical system 32 (see FIG. 2) such that the entire target optical surface 13 is subjected to a laser intensity between $10^{-2}$ to $10^{-1}$ that for which operation is desired. The points 36 from which photoelectrons are emitted are then displayed on the fluorescent screen 44 in an image 46 of the target optical surface 13 and are pinpointed. (The inventor has used a Galileo model 6025 multiplier array 42, 43 with a phosphorous screen 44 as the imaging apparatus.)

The electrostatic lens array 41 may then be adjusted via it control means 45 so as to create the electric field desired for photo-ion identifications. The laser beam 34 may then be focused to the small intense spot 35 required for photo-ion detection and the target optical surface 13 moved by the moving apparatus such that selected points are subjected to sufficient laser intensity to induce photo-ionization of surface impurities present on the target optical surface 13. The timer 24 is now operably connected to the electrostatic plate 46 and is operated in conjunction with the laser pulse as before. The calculations are made in a similar manner as before, but are somewhat complicated by the more complex electric field pattern created by the electrostatic lens array 41. Mollenstadt, et al, supra, provides a description of the calculations required in order to determine the electric field strengths acting on the charged particles for such lens arrays.

By slightly modifying either of these configurations, the apparatus may be used to "cleanse" the optical surface 13 of impurities. The timer 24 is disconnected. The laser device is focused via the optical system 32 to deliver an intense narrow beam 34, in order to induce photo-ion emission, as previously described. The photoelectric detector 22 is set to attract and detect photo-ions. The target optical surface 13 is then moved such that a point of identified surface impurity is hit by the laser beam (at 35).

The laser device may then be operated in either a continuous or pulsed mode, depending upon the power requirements or capacity of the system. The intensity must be adequate to induce photo-ion emission. The laser device 31, then, is operated continuously (or repeatedly pulsed) until photo-ion emission from that point 35 on the target optical surface 12 ends. The point 35 then, may be said to have been cleared of the surface impurity.

In an alternate embodiment of the invention, it is used merely to pretest the optical device 14 for use at a given wavelength and intensity. The recorder 21, is operably connected to the moving means 12 and the photoelectric detector 22. The biasing means 23 has been adjusted to attract and detect photoelectrons via a positive electric field 36.

A laser device 31, with output at the exact wavelength for which use of the optical device 14 is desired, is used and focused such that the widest possible beam 34 to have an intensity of $10^{-1}$ that for which use of the optical device 14 is desired. The moving apparatus 12 is then used to move the target optical surface 13 until the entire surface 13 has been exposed to the laser beam 35.

If the recorder 21 does not show an adequate level of photoelectron emission to indicate an undesirably low damage threshold, the optical device 14 is cleared for the desired use as optical damage occurs at the incident surface 13 first, and this surface has demonstrated its ability to operate successfully at that intensity.

Described, then, have been embodiments of the invention permitting low power location of weak spots and identification of surface impurities; high speed performance of the same operations; cleansing of the optical surface; and simple pretesting of an optical device.

While embodiments of the invention have been shown and described, further embodiments or combinations of those described herein will be apparent to those skilled in the art without departing from the invention. For example, it is additionally possible to perform high speed simple pretesting by utilizing the imaging apparatus (FIG. 3) at a high enough laser intensity and the proper wavelength to satisfy the pretesting conditions. The power requirements for such a configuration however, are within one or two orders of ten of that for which ultimate operation of the device is desired.

What is claimed is:

1. A method for examining an optical surface having a predetermined normal operating power level and frequency to identify discrete areas that are damage prone, due to impurity in the area, at the normal operating power level and frequency of the surface, and for removing the impurity from one or more of the damage prone areas, including the steps of:

directing a laser beam at the optical surface, said bean having a power level from $10^{-2}$ to $10^{-1}$ of the normal operating power level, the frequency of said beam being at or very near the frequency to be used at the normal operating power level;

detecting the photoelectric emission from the damage prone areas of the optical surface to identify the damage prone areas;

focusing, directing and holding the laser beam sequentially on the impurity of the damage prone areas so as to ionize particles of the impurity, the intensity of the laser beam being at a level that is sufficient to ionize the impurity particles but is below the damage threshold of the optical surface, the frequency of the laser beam being at or very near the frequency to be used at the normal operating power level of the surface; and drawing the ionized impurity particles off of the optical surface with an electric field.

2. The method of claim 1, further including the steps of:

enclosing the optical surface to be examined within a common vacuum with a photoelectric detector which has been biased to attract and measure photoelectrons emitted from the optical surface to be examined;

probing the optical surface with the laser beam;

measuring and recording the photoelectron emission from all points on the optical surface as a result of the probing laser beam; and identifying those areas for which the photoelectron emission indicates a low damage threshold.

3. The method of claim 1, further including the steps of:

enclosing the optical surface to be tested within a common vacuum with a photoelectronic detector biased to attract and measure photoelectrons emitted from the optical surface to be examined, thoroughly examining the optical surface with the laser beam; and detecting and measuring photoelectronic emission from the optical surface as a result of the examining laser beam in an amount sufficient to indicate a damage threshold on the otpical surface that is below the noraml operating intensity for which the optical surface is being tested.

4. The method of claim 1, wherein the laser beam is scanned over the optical surface.

5. The method of claim 1, wherein the beam is focused on the entire surface.

6. The method of claim 1, further including the steps of, defining the electric field acting on the ionized impurity particles and measuring the time of the flight of the ionized particles through a known distance within the electric field so as to ascertain the mass to charge ratio of the ionized impurity particles.

7. The method of claim 5, further including the step of, subjecting the moving ionized particle to a magnetic field and observing the deflection of the ionized particle in order to determine the precise charge on the ionized impurity particle.

8. The method described in claim 2 in order to detect the presence of impurities on the identified weak spots, additionally including the steps of;

reversing the bias of the photoelectric detector so as to attract and measure photo-ion emission by creating a negative electric field of known strength from the optical surface to the photoelectric detector;

probing those areas from which photoelectron emission was detected with a focused laser beam of intensity sufficient to induce photo-ion emission but not sufficient to damage the vacuum enclosed optical surface; and detecting and measuring the amount of photo-ion emission from the identified weak spots or damage prone areas of the vacuum enclosed optical surface.

9. The method described in claim 8 to allow the identification of the impurities detected on the vacuum enclosed optical surface, including the steps of;

timing the flight of the emitted photo-ions from the optical surface to the photoelectric detector;

calculating the mass to charge ratio of the emitted photo-ion from knowledge of the electric field strength acting on the emitted photo-ions by the photoelectric detector and the time of flight of the emitted photo-ions from the vacuum enclosed optical surface to the photoelectric detector; and deducing the identity of the emitted photo-ion.

10. The method described in claim 2, additionally including the steps of:

directing a focused laser beam of intensity sufficient to induce photo-ions emission but not sufficient to damage the optical surface to the points at which surface impurities have been located; and maintaining the focused laser on the weak spot for as long as photo-ion emission is detected by the photoelectric detector.

11. The method of claim 1 wherein said laser beam is a pulsed beam.

* * * * *